United States Patent [19]
Mizuno

[11] Patent Number: 6,072,178
[45] Date of Patent: Jun. 6, 2000

[54] SAMPLE ANALYZING APPARATUS

[75] Inventor: Fumio Mizuno, Tokorozawa, Japan

[73] Assignee: Hitachi, Ltd., Tokyo, Japan

[21] Appl. No.: 09/014,384

[22] Filed: Jan. 27, 1998

[30] Foreign Application Priority Data

Jan. 29, 1997 [JP] Japan .................................. 9-014923

[51] Int. Cl.$^7$ ............................ H01J 37/28; G01N 23/00
[52] U.S. Cl. ........................... 250/310; 250/307; 250/399
[58] Field of Search ..................................... 250/309, 310, 250/307, 397, 399

[56] References Cited

U.S. PATENT DOCUMENTS

| | | | |
|---|---|---|---|
| 3,812,288 | 5/1974 | Walsh et al. | 250/310 |
| 4,620,284 | 10/1986 | Schnell et al. | 364/498 |
| 5,142,149 | 8/1992 | Isakazawa et al. | 250/310 |
| 5,453,613 | 9/1995 | Gray et al. | 250/281 |
| 5,483,065 | 1/1996 | Sato et al. | 250/310 |
| 5,596,195 | 1/1997 | Obori et al. | 250/310 |
| 5,659,172 | 8/1997 | Wagner et al. | 250/307 |
| 5,866,903 | 2/1999 | Morita et al. | 250/310 |
| 5,945,833 | 8/1999 | Mil'shetin et al. | 250/310 |

*Primary Examiner*—Bruce C. Anderson
*Attorney, Agent, or Firm*—Kenyon & Kenyon

[57] ABSTRACT

The invention provides a sample analyzing apparatus to identify a particle accurately, securely and rapidly. After a wafer is pre-aligned and its wafer number is read, a recipe is read. The wafer is carried to an XY stage and aligned. A wafer map is read and displayed. An operator specifies a particle desired to be analyzed of particles on the wafer and moves a stage so that that particle is just below an electron beam. A scanning electron beam is irradiated over the specified particle so as to form an SEM image. The SEM image is compared to a corresponding reference SEM image and a precision positioning of the specified particle is carried out. The electron beam is irradiated to the specified particle and an emitting characteristic X-ray is detected. Its spectrum is displayed. The spectrum is compared to the reference spectrum and then reference spectrums estimated to be the same are listed up.

24 Claims, 3 Drawing Sheets

(1) CASE WHEN ALL PEAK POSITIONS OF REFERENCE SPECTRUM ARE INCLUDED IN PEAK POSITIONS OF OBSERVED SPECTRUM (2) CASE WHEN ALL PEAK POSITIONS OF OBSERVED SPECTRUM ARE INCLUDED IN PEAK POSITIONS OF REFERENCE SPECTRUM

SAMPLE ANALYZING APPARATUS

BACKGROUND OF THE INVENTION

1. Field of the Invention

This invention relates to a sample analyzing apparatus and more particularly to such a sample analyzing apparatus as a scanning electron microscope (referred to as "SEM") equipped with energy diffusion type X-ray analyzer (referred to as "EDX") and a laser mass spectrometer.

2. Description of the Related Art

A typical application field of the present invention is semiconductor production. In semiconductor production, the particle on wafer is one of the largest causes for determining product yield. To make a countermeasure for reduction of adhering particles and carry out it, it is necessary to find a generation source of the particles To find out the generation source of the particles, obtaining information of particle composition is an effective weapon. For the particle composition analysis, SEMs with Energy Dispersive X-ray Spectroscopy analysis capability has been widely used. When the composition analysis on the particle on the wafer is carried out by SEMs with Energy Dispersive X-ray Spectroscopy analysis capability, for example, following processes are carried out.

A wafer to be measured taken out of a wafer cassette is pre-aligned with reference to an orientation flat or notch of the wafer. The pre-alignment is an operation of aligning a crystal direction of the wafer with a traveling direction of the XY stage. After the pre-alignment is performed, the wafer is carried to the XY stage in a sample chamber kept in vacuum condition and mounted thereon. The wafer mounted on the XY stage is aligned by means of an optical microscope mounted on a top face of the sample chamber. The alignment is an operation for correction between the coordinate systems of a pattern formed on the wafer and stage coordinate systems. Concretely, an optical microscope image magnified several hundreds times of the alignment pattern formed on the wafer is compared to a reference image of the alignment pattern preliminarily registered, and stage position coordinates are adjusted so that that magnified optical microscope image overlaps the reference image. After the alignment, the wafer is moved to a particle to be analyzed. After the wafer is moved to the particle position, electron beam is irradiated thereover and X-ray spectrum is formed and displayed. By observing the X-ray spectrum, an observer determines and identifies the composition of the particle with reference to knowledge and information possessed by him.

However, according to such a method, if the operator is not an expert, a standard of determining the composition becomes obscure, so that a result of identification is not reliable, and further it takes long to analyze.

SUMMARY OF THE INVENTION

It is an object of the present invention to provide a sample analyzing apparatus suitable for identifying a particle accurately, securely and rapidly regardless of knowledge and skill of the operator.

According to the present invention, there is provided a sample analyzing apparatus for generating a spectrum by analyzing a sample, which registers reference spectrums as a library; reads a registered reference spectrum; compares the read reference spectrum with the generated spectrum; and selects a reference spectrum estimated to be the same as the generated spectrum.

DETAILED DESCRIPTION OF THE PREFERRED EMBODIMENTS

Figure 1:
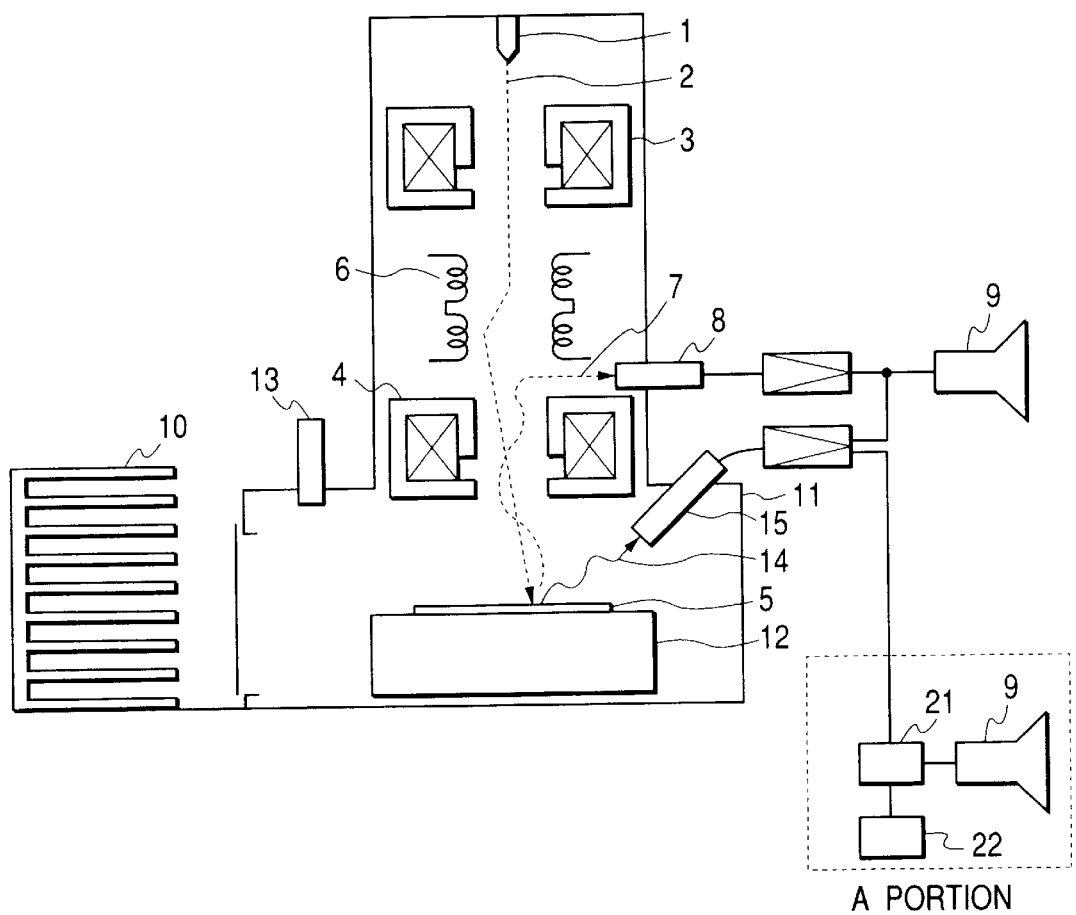
FIG. 1 is a basic composition of an embodiment of SEM wits Energy Dispersive X-ray Spectroscopy analysis capability as a sample analyzing apparatus according to the present invention.

FIG. 1 shows a basic structure of an embodiment of the SEM with Energy Dispersive X-ray Spectroscopy analysis capability as a sample analyzing apparatus according to the present invention. Electron beam 2 emitted from an electron gun 1 is focused by a condenser lens 3 and an objective lens 4 so as to form a focal point on a plane of a wafer 5 which is a sample. The electron beam 2 is warped by a deflector 6 so as to perform two-dimensional or single dimensional scanning of the wafer surface.

On the other hand, the wafer irradiated by the electron beam 2 emits secondary electrons 7 and characteristic X-ray 14. The secondary electrons 7 are detected by a secondary electron detector 8, converted to electric signals and subjected to amplification or the like. After that processing, the electric signals are used for brightness modulation or amplitude modulation. The display 9 is scanned in synchronism with scanning of the wafer surface by the electron beam 2. In a case when the two-dimensional scanning is performed to carry out brightness modulation, a sample image (SEM image) is formed on the display. In a case when the single dimensional scanning is performed so as to carry out amplitude modulation, a line profile is formed thereon.

The characteristic X-ray 14 is detected by a semiconductor X-ray detector 15 and subjected to energy analysis. Then, X-ray spectrum is formed on the display 9. This method is called energy diffusion type X-ray analysis (referred to as "EDX").

Figure 2:
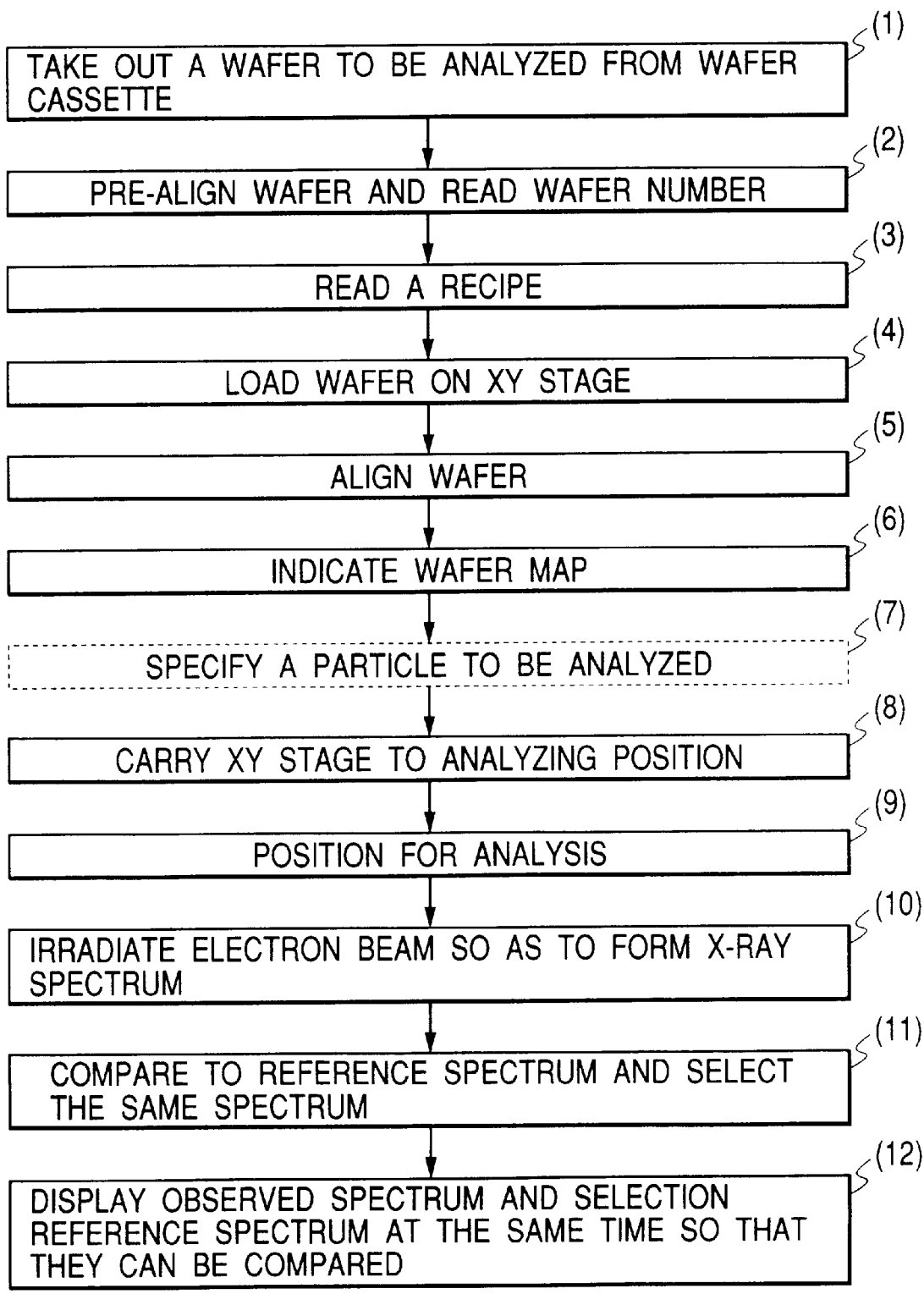
FIG. 2 is a diagram showing an example of flow of analytic procedure of the present invention.

According to the present invention, FIG. 2 shows an example of a flow of analysis procedures that are numbered from 1 to 12. A wafer 5 to be measured is taken out of a wafer cassette 10 (1). The wafer 5 is pre-aligned and at the same time, a wafer identification number formed on the wafer is read by a wafer number reader (not shown) (2). The wafer number is inherent in each wafer. Based on a read wafer number, a recipe preliminarily registered corresponding to this wafer is read out (3). The recipe determines the analysis procedure and condition of this wafer. A subsequent operation is automatically or semi-automatically carried out according to this recipe. A following description is about a case of semi-automatic operation.

After the recipe is read, the wafer 5 is carried onto a XY stage 12 in the sample chamber 11 kept in vacuum condition (4). The wafer 5 loaded on the XY stage 12 is aligned using an optical microscope 13 mounted on a top of the sample chamber 11 (5). In this alignment, an optical microscope image magnified several hundreds times of an alignment pattern formed on the wafer 5 is compared to a reference image of the alignment pattern preliminarily registered and the stage position coordinates are corrected so that the magnified optical microscope image overlaps the reference image.

After the alignment is carried out, a wafer map preliminarily registered corresponding to this wafer is read and indicated on the display (6). The wafer map indicates a position and size of the particle existing on this wafer. After the wafer map is indicated, an operator specifies a particle to be analyzed from particles shown on the wafer map (7). If the particle to be analyzed is specified, the wafer 5 to be measured is carried by the stage so that the specified particle is just below the electron beam (8). After that, scanning electron beam is irradiated over the specified particle so as to form the SEM image. The SEM image is compared to the reference SEM image preliminarily registered corresponding to the specified analysis point like in the alignment operation, and then precision positioning of the specified particle is carried out so that that SEM image overlaps the reference SEM image (9). The positioning is carried out by minute adjustment of the scanning area by the electron beam.

When the positioning of the wafer is completed, the specified particle is located almost in the center of the screen. With this condition, electron beam is irradiated over the specified particle all at once and the emitting characteristic X-ray is detected. A spectrum of the detected X-ray is displayed on the display (10). On the other hand, the detected X-ray spectrum is compared to the reference spectrum whose peak position and peak height order are registered preliminarily in a library and a reference spectrum estimated to be the same is listed up (11).

Figure 3:
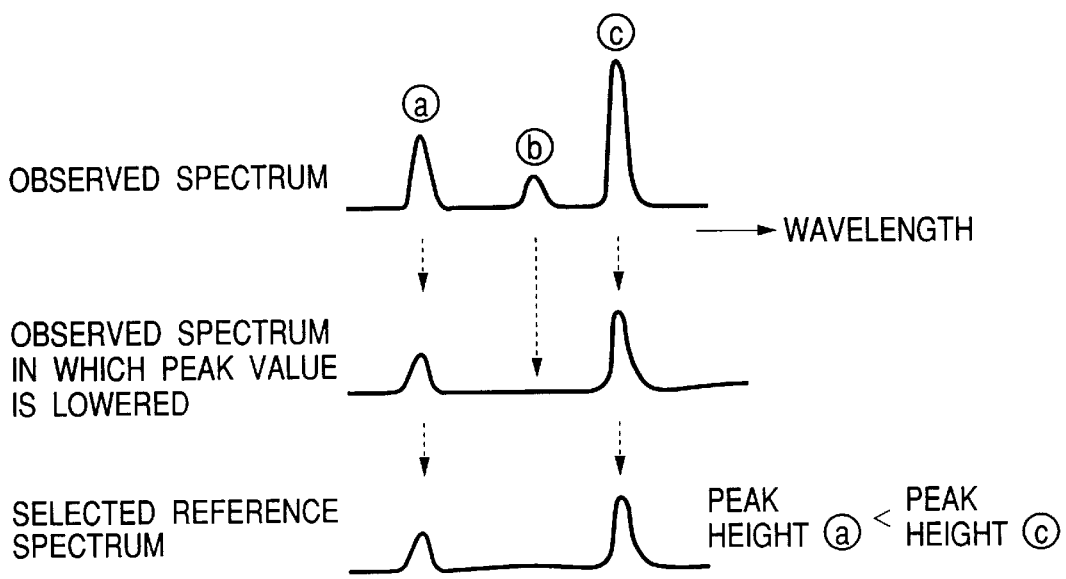
FIG. 3 is an explanatory view about spectrum selection according to the present invention.
Figure 3:
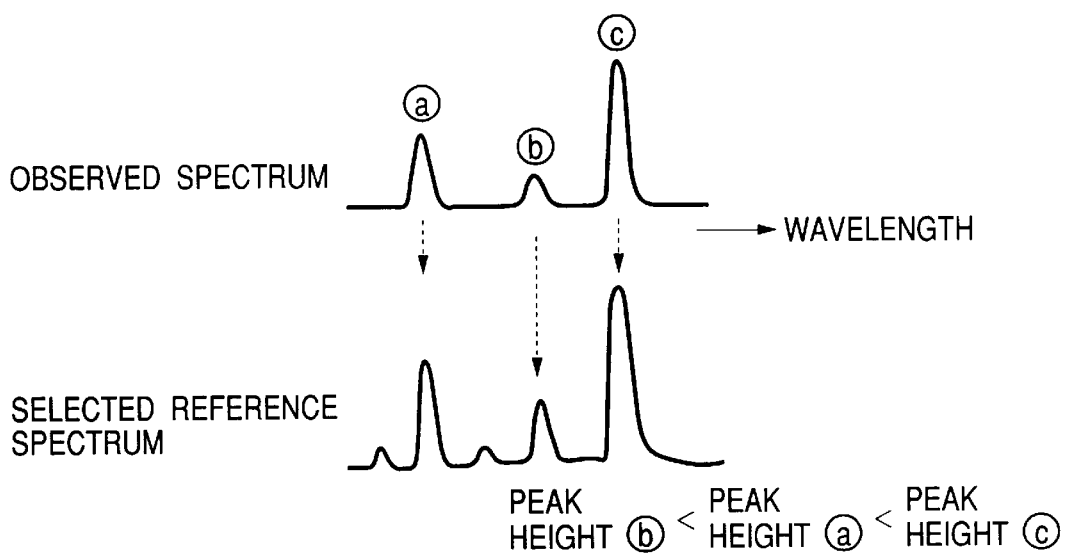

For the comparison and listing, for example, a hardware composition shown in portion A of FIG. 1 is used. Using a processor 21, a detected X-ray spectrum is overlapped with the reference spectrum for comparison (12). The detected X-ray spectrum is compared by overlapping with a reference spectrum read from a memory 22 by changing the spectrum height as shown in FIG. 3.

Listed reference spectrums are displayed on a display with their additional information. The additional information is sample condition such as material name which falls under that spectrum and names of process/equipment in which that material is used. The additional information is stored in the memory 22 together with tables of the reference spectrum, peak position and height order.

There is a case in which a plurality of spectrums estimated to be the same are listed up. By inputting the additional information of an observed wafer such as a current process name, process equipment, history and the like of the observed wafer, the number of the wafers estimated to be the same can be further narrowed down.

In a case when a plurality of spectrums estimated to be the same are listed, the observed spectrum is compared with a reference spectrum estimated to be the same. If that comparison is displayed, an operator can narrow down the same spectrums easily. As for displaying of the comparison, to facilitate comparison and determination of difference between two spectrums, color indication, for example, indicating a different portion between the two in red, is employed.

To facilitate narrowing down of the same spectrums, as additional information of the recipe, optical microscope images, focused ion beam images and various analysis data corresponding to the particle are filed. At the time of analysis, these images and analysis data can be read and displayed as reference information.

After the analysis of the specified particle is completed, the wafer map is displayed on the display again. The operator inputs analysis end, analysis result and selection result onto the specified particle in the wafer map so that they are displayed and details of the analysis result are stored in analysis database file.

An analysis of a position is completed as described above. If there is a particle left to be analyzed, a new particle is specified on the wafer map and after the specified particle position is changed, the operation shown in FIG. 2 is repeated.

The analysis work for a single wafer is completed. If there are plural wafers to be analyzed left in the wafer cassette, a next wafer is taken out of the wafer cassette and the analysis is repeated according to the steps shown in FIG. 2.

In this analysis, the operator specifies a particle, that is, an analysis point indicated on the wafer map each time during the procedure, it is permissible to employ automatic analysis of automatically proceeding to a preliminarily specified analysis point for performing analysis gradually.

In this process, after the reference spectrum estimated to be the same is selected, it is indicated with an observed spectrum so as to identify a particle, it is permissible to omit the confirmation by the simultaneous indication and automatically proceed following processing.

The reference spectrum can be registered additionally or again even during analysis procedure.

Here, as the reference spectrum, a spectrum preliminarily registered before the procedure is used. However, if an observed spectrum does not coincide with any reference spectrum so that it can be considered as a new substance or the observed spectrum is more suitable as a reference spectrum as compared to a conventional reference spectrum, the observed spectrum is added or registered to the reference spectrums. The newly registered spectrum can be used to classify subsequent analysis result even if its substance name has not been detected.

Although the case in which a single spectrum is picked up for a single particle is indicated here, it is permissible to collect a plurality of spectrums for a single particle. This corresponds to a case in which different electron beam irradiation condition or different measurement position data are required.

For such a sample which takes long until charge-up is saturated when charged particle beam, such as electron beam or ion beam is used, after irradiation with the charged particle beam for a predetermined time interval, its observed image should be obtained.

As for the simultaneous indication of the observed spectrum and reference spectrum, it is permissible to display them in divided area of the same display or to indicate them on separate displays.

There has been indicated such a method in which, after a wafer is aligned with a low magnification luminous image, its position is determined based on a high magnification SEM image. However, it is also permissible to provide with a function of detecting a specified particle directly according to the high magnification SEM image, and if there is no specified particle found, searching for any other particle in the neighborhood.

Although the XY stage is used here, if XYT (T means a tilt) is used instead of the XY stage, analysis of particles adhering to a pattern wall is facilitated.

Although a patterned wafer is considered as an observation object here, it is also possible to analyze a particle adhering to a bare wafer. In this case, for the positioning of a particle to be analyzed, the neighborhood search method is used. The analysis object is not restricted to any particle, but may be fault such as pattern defect.

Further, the analysis object is not restricted to the semiconductor wafer. The sample is not restricted to any particular type, but permitted to be wafers for pick-up device or display device. Other configurations than the wafer are also permitted.

Although spectrum formation by electron beam is used here, it is permissible to use physical analytic means by ion beam or optical beam and it is also permissible to use chemical analytic means such as atomic absorption spectroscopy and mass spectrometric analysis.

Although scanning image is used for alignment, it is permissible to use an image formed by focusing optical system.

According to the embodiment of the present invention as evident from the above description, the particle can be identified accurately, securely and rapidly regardless of knowledge and skill of the operator.

Further, by using the additional information such as sample condition, it is possible not only to identify substance but also detect an occurrence place, time and the like easily and rapidly.

The present invention is capable of providing a sample analyzing apparatus suitable for identifying substance accurately, securely and rapidly, regardless of knowledge and skill of the operator.

What is claimed is:

1. An apparatus for inspecting semiconductor devices on the basis of a secondary signal obtained by irradiating said devices with an energy beam comprising:

a memory storing recipes including data associated with analytical positions on said semiconductor devices, and a plurality of reference spectra to be used to identify the materials at said analytical positions;

apparatus directing said energy beam onto one of said analytical position on one of said semiconductor devices;

a detector detecting said secondary signal;

a processor programmed to read said data of said analytical position, generate a spectrum on the basis of said detected secondary signal, compare said generated spectrum and said plurality of reference spectra, and select a reference spectrum estimated to be the same as said generated spectrum.

2. An apparatus according to claim 1, and further including a display displaying said generated spectrum and said selected spectrum at the same time.

3. An apparatus according to claim 2, wherein said processor is further programmed to:

compare peak positions and peak height order of said generated spectrum with those of said reference spectrum, and select the coinciding reference spectrum as a same spectrum when the peak positions of one spectrum includes all peak positions of another spectrum and the peak orders of both the spectra coincide with each other.

4. An apparatus according to claim 2, wherein said processor is further programmed to use additional information including a sample condition as well as the spectrum as a factor for the selection of the same spectrum as a spectrum generated from said reference spectrum.

5. An apparatus according to claim 2, wherein said processor is further programmed to store the reference spectrum during analytic operation.

6. An apparatus according to claim 1, wherein said display displays said generated spectrum and said selected spectrum so as to overlap each other.

7. An apparatus according to claim 6, wherein said processor is further programmed to:

compare peak positions and peak height order of said generated spectrum with those of said reference spectrum, and select the coinciding reference spectrum as a same spectrum when the peak positions of one spectrum includes all peak positions of another spectrum and the peak orders of both the spectra coincide with each other.

8. An apparatus according to claim 6, wherein said processor is further programmed to use additional information including a sample condition as well as the spectrum as a factor for the selection of the same spectrum as a spectrum generated from said reference spectrum.

9. An apparatus according to claim 6, wherein said processor is further programmed to store the reference spectrum during analytic operation.

10. An apparatus according to claim 1, wherein said processor is further programmed to:

compare peak positions and peak height order of said generated spectrum with those of said reference spectrum, and select the coinciding reference spectrum as a same spectrum when the peak positions of one spectrum includes all peak positions of another spectrum and the peak orders of both the spectra coincide with each other.

11. An apparatus according to claim 10, wherein said processor is further programmed to store the reference spectrum during analytic operation.

12. An apparatus according to claim 10, wherein said apparatus directing said energy beam comprises a probe in the form of a charged particle beam and a deflector causing said beam to be scanned over said device in a specified time interval so as to form an image.

13. An apparatus according to claim 1, wherein said processor is further programmed to use additional information including a sample condition as well as the spectrum as a factor for the selection of the same spectrum as a spectrum generated from said reference spectrum.

14. An apparatus according to claim 1, wherein said processor is further programmed to store the reference spectrum during an analytic operation.

15. An apparatus according to claim 14, wherein said processor is further programmed to use additional information including a sample condition as well as the spectrum as a factor for the selection of the same spectrum as a spectrum generated from said reference spectrum.

16. An apparatus according to claim 1, wherein said apparatus directing said energy beam comprises a probe in the form of a charged particle beam and a deflector causing said beam to be scanned over said device in a specified time interval so as to form an image.

17. A method for inspecting a sample on the basis of a secondary signal obtained by irradiating said sample with an energy beam by performing steps (13)–(15) and at least one of the remaining of steps (1)–(18), said steps comprising:

(1) pre-aligning said sample;

(2) storing a recipe for carrying out analysis of said sample;

(3) reading a sample number formed on said sample;

(4) reading the recipe based on the read sample number;

(5) carrying out analysis based on the read recipe;

(6) storing a reference image for alignment;

(7) forming said reference image for alignment and carrying out alignment of said sample by comparing the reference image with the alignment pattern image of said sample;

(8) preliminarily storing an analytic point map of said sample;

(9) reading and indicating the registered analytic point map;

(10) moving said sample according to a specification on the analytic point map or an instruction of the recipe so as to set the specified or instructed analytic point at a desired position;

(11) storing a reference image of the specified or instructed analytic point;

(12) forming a positioning image of the specified or instructed analytic point and positioning said analytic point by verifying the positioning image of the specified or instructed analytic point with a positioning reference image of said analytic point;

(13) generating a spectrum by analyzing the positioned analytic point;

(14) storing a library of reference spectra;

(15) selecting a reference spectrum estimated to be the same as said generated spectrum;

(16) displaying the reference spectrum estimated to be the same and said generated spectrum at the same time;

(17) displaying the reference spectrum estimated to be the same and said generated spectrum so that they overlap each other; and

(18) displaying and/or filing an analysis result of said analytic point and the selection result.

18. A method according to claim 17, and further comprising using additional information including sample condition as well as the spectrum as a factor for the selection of the same spectrum as a spectrum generated from said reference spectrum.

19. A method according to claim 18, comprising scanning a probe in the form of a charged particle beam over said sample device in a specified time interval so as to form an image.

20. A method according to claim 17, and further including storing the reference spectrum during analytic operation.

21. An apparatus for inspecting semiconductor devices on the basis of a secondary signal obtained by irradiating the devices with an energy beam comprising:

means for generating a spectrum on the basis of said secondary signal;

means for storing a plurality of reference spectra for identifying materials in said devices;

means for displaying said generated spectrum and at least one reference spectrum;

means for modifying said generated spectrum about height of spectrum and/or position of spectrum.

22. An apparatus for inspecting semiconductor devices on the basis of a secondary signal obtained by irradiating said devices with an energy beam comprising:

means for generating a spectrum on the basis of said secondary signal;

means for storing a plurality of reference spectra for identifying materials in said devices;

means for inputting information relating to a manufacturing process;

means for limiting the number of reference spectra on the basis of said input information;

means for comparing said generated spectrum with the limited number of reference spectra.

23. An apparatus for inspecting semiconductor wafers on the basis of a secondary signal obtained by irradiating said semiconductor wafers with an energy beam comprising:

means for displaying a map of said wafer and particles placed on said wafer;

means for choosing said particles on said map;

means for irradiating said energy beam on said chosen particles;

means for detecting the secondary signal obtained by irradiating said chosen particles;

means for generating a spectrum on the basis of said detected secondary signal;

means for storing a plurality of reference spectra for identifying the materials of said particle;

means for comparing said generated spectrum and said a plurality of reference spectra;

means for selecting a reference spectrum estimated to be the same as said generated spectrum.

24. A method for inspecting semiconductor devices on the basis of a secondary signal obtained by irradiating said devices with an energy beam after the manufacturing process of said semiconductor devices comprising:

(a) reading a recipe including data associated with analytical positions on said semiconductor devices;

(b) positioning an irradiating point of said energy beam at one of said analytical positions;

(c) detecting said secondary signal obtained on basis of irradiation of said energy beam;

(d) repeating steps (a)–(c) for a plurality of analytical positions;

(d) generating a spectrum on the basis of said secondary signal for each of a plurality of said analytical positions;

(e) comparing said generated spectra and a preregistered plurality of reference spectra;

(f) determining of what material a particle is made on the basis of a reference spectrum estimated to be the same as said generated spectrum.

* * * * *